US 6,746,840 B1

(12) United States Patent
Neriishi

(10) Patent No.: US 6,746,840 B1
(45) Date of Patent: Jun. 8, 2004

(54) MICRO ARRAY AND ANALYZING METHOD USING THE SAME

(75) Inventor: Keiko Neriishi, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/624,395

(22) Filed: Jul. 24, 2000

(30) Foreign Application Priority Data

Jul. 26, 1999 (JP) ............................................ 11-211308

(51) Int. Cl.[7] .............................. C12Q 1/68; C12M 1/00; G01N 15/06
(52) U.S. Cl. ........................ 435/6; 435/174; 435/283.1; 435/287.2; 422/50; 422/68.1
(58) Field of Search ........................ 435/6, 287.2, 174, 435/283.1; 422/56, 68.1

(56) References Cited

U.S. PATENT DOCUMENTS 4,617,468 A * 10/1986 Shiraishi et al. ......... 250/484.1
5,632,957 A * 5/1997 Heller et al. ............... 422/68.1

OTHER PUBLICATIONS

Davis et al. Basic Methods in Molecular Biology, DNA Hybridization, 1986, pp. 84–87.*

* cited by examiner

Primary Examiner—B J Forman
(74) Attorney, Agent, or Firm—Sughrue Mion, PLLC

(57) ABSTRACT

A micro array, which comprises a stimulable phosphor sheet, and multiple kinds of biomolecules arrayed and fixed on the stimulable phosphor sheet, is prepared. A biomolecule labeled with an energy generating substance is brought into contact with the micro array and is subjected to hybridization with a fixed biomolecule, which is among the multiple kinds of the biomolecules fixed on the stimulable phosphor sheet. The stimulable phosphor sheet is caused to store energy from the energy generating substance acting as the label of the labeled biomolecule having been hybridized with the fixed biomolecule. The stimulable phosphor sheet is then exposed to stimulating rays, a which cause it to emit light in proportion to the amount of energy stored thereon. The emitted light is photoelectrically detected, and the fixed biomolecule having been hybridized with the labeled biomolecule is thus detected.

14 Claims, 3 Drawing Sheets

F I G . 1
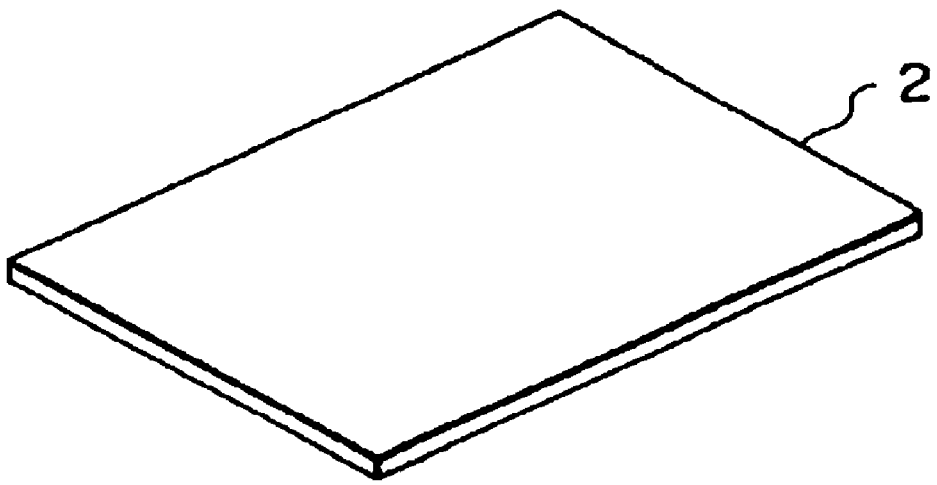

MICRO ARRAY AND ANALYZING METHOD USING THE SAME

BACKGROUND OF THE INVENTION

1. Field of the Invention

This invention relates to a micro array and an analyzing method using the micro array. This invention particularly relates to a micro array, which comprises a base plate and multiple kinds of biomolecules arrayed and fixed on the base plate. This invention also relates to an analyzing method using the micro array, wherein the micro array is subjected to hybridization with a solution containing a labeled biomolecule, and a biomolecule fixed on the base plate of the micro array, which biomolecule has been hybridized with the labeled biomolecule, is specified.

As will be described later, the term "micro array" as used herein has broad meanings embracing a micro array, a macro array, a DNA chip, and others.

2. Description of the Prior Art

A thesis entitled "DNA microarray for gene expression analysis" is published in Experimental Medicine Series, Yodosha Co., Vol. 17, the January 1999 issue, pp. 61–65. In the thesis, a technique for performing a genetic expression analysis by the utilization of a micro array is explained in detail.

Recently, the genetic expression analyzing techniques utilizing micro arrays have widely been used in practice. As illustrated in FIG. 6, in the genetic expression analyzing techniques, a micro array comprising a base plate 40 and multiple kinds of biomolecules arrayed and fixed in a matrix-like form on the surface of the base plate 40 is utilized. The base plate 40 is constituted of a membrane, a glass, a slide glass, a silicon base plate, or the like. As the multiple kinds of biomolecules, currently, cDNA, oligo-DNA, other DNA's, PNA, EST, and the like, are utilized. The micro array comprising the base plate 40 and multiple kinds of biomolecules arrayed and fixed in a matrix-like form on the surface of the base plate 40 is referred to as the macro array, the micro array, the DNA chip, or the like, depending on the kind of the base plate 40, and the like. In this specification, the group of the macro array, the micro array, the DNA chip, and the like, is generically referred to as the "micro array."

Also, in the genetic expression analyzing techniques utilizing micro arrays, various kinds of biomolecules, such as cDNA, genome DNA, mRNA, total RNA, other RNA's, dNTP, and PNA, which have been labeled with a radioactive isotope, a fluorescent substance, or the like, are prepared.

Thereafter, the biomolecules, which have been fixed in a matrix-like form on the surface of the base plate 40, and a biomolecule, which has been labeled with the radioactive isotope, the fluorescent substance, or the like, are subjected to hybridization.

In cases where the biomolecules having been fixed on the surface of the base plate 40 contains a biomolecule, which is capable of undergoing hybridization (binding) with the biomolecule having been labeled with the radioactive isotope, the fluorescent substance, or the like, the fixed biomolecule and the labeled biomolecule are hybridized with each other on the base plate 40. As a result, the radioactive isotope, the fluorescent substance, or the like, is fixed at a position on the base plate 40, at which the fixed biomolecule having been hybridized with the labeled biomolecule is located. Also, the radioactive isotope, the fluorescent substance, or the like, is not fixed at positions on the base plate 40, at which the fixed biomolecules having not been hybridized with the labeled biomolecule are located. In FIG. 6, the circles surrounding the dots indicate the positions on the base plate 40, at which the fixed biomolecule having been hybridized with the labeled biomolecule is located, i.e. the positions at which the radioactive isotope, the fluorescent substance, or the like, has been fixed to the base plate 40. FIG. 6 is a conceptual view, in which the dots located in a matrix-like form can be visually discriminated from one another. However, actually, fine dots are located at a high density on the base plate 40, and therefore they cannot be visually discriminated from one another.

In cases where the label is the radioactive isotope, a stimulable phosphor sheet capable of storing energy from radiation thereon may be utilized in order to detect the positions on the base plate 40 at which the radioactive isotope is located.

When the stimulable phosphor sheet is exposed to radiation radiated out from the radioactive isotope, the stimulable phosphor sheet stores energy from the radiation. When the stimulable phosphor sheet, on which the energy from the radiation has been stored, is exposed to stimulating rays, such as a laser beam, which cause the stimulable phosphor sheet to emit light in proportion to the amount of energy stored thereon during its exposure to the radiation, light is emitted by the stimulable phosphor sheet. At this time, no light is emitted from the sites, which were not exposed to the energy from the radiation. One of typical stimulable phosphor sheets comprises a substrate and a stimulable phosphor layer, which is overlaid on the substrate and comprises a binder and BaFX phosphor particles dispersed at a high density in the binder, where X represents a halogen. The stimulable phosphor sheet is also known as a radiation image storage panel utilizing a stimulable phosphor.

As illustrated in FIG. 7, the stimulable phosphor sheet (also referred to as the imaging plate) IP is brought into close contact with the surface of the base plate 40, on which the radioactive isotope has been locally fixed as a result of the hybridization. In this manner, the stimulable phosphor sheet is exposed locally to the radiation radiated out from the radioactive isotope. In FIG. 7, the base plate 40 is turned upside down from the state of FIG. 6 and is then brought into close contact with the stimulable phosphor sheet IP.

As a result, the stimulable phosphor sheet IP is exposed locally to the radiation. The stimulable phosphor sheet IP, on which the energy from the radiation has been stored, is then exposed to the stimulating rays and is caused to locally emit light. In accordance with the position which emits the light, the position on the base plate 40, at which the fixed biomolecule having been hybridized with the labeled biomolecule is located, can be specified. Also, in accordance with the thus specified position, the kind of the fixed biomolecule, which has been hybridized with the labeled biomolecule, can be specified. FIG. 8 is an explanatory view showing the read-out step, which is performed in the manner described above. In FIG. 8, the circle indicates the site on the stimulable phosphor sheet IP, which was locally exposed to the radiation coming from the radioactive isotope and has stored the energy from the radiation. Also, in FIG. 8, reference numeral 41 represents the stimulating rays, and reference numeral 42 represents the light emitted from the site on the stimulable phosphor sheet IP.

When the stimulable phosphor sheet IP is exposed to the stimulating rays and is caused to emit the light, the site at which the energy from the radiation has been stored returns to the state in which no energy from the radiation was stored. Therefore, the stimulable phosphor sheet IP can be used repeatedly. However, as illustrated in FIG. 7, with the conventional technique described above, the processing must be performed for accurately setting the position of the stimulable phosphor sheet IP with respect to the base plate 40, and bringing the entire area of the stimulable phosphor sheet IP into close contact with the base plate 40 and thus superposing the entire area of the stimulable phosphor sheet IP upon the base plate 40. Therefore, the conventional technique described above has the problems in that considerable time and labor are required to perform the processing. Also, with the conventional technique described above, it is necessary to perform the step for bringing the stimulable phosphor sheet IP into close contact with the base plate 40 and causing the energy from the radiation to be stored on the stimulable phosphor sheet IP. Therefore, the conventional technique described above has the drawbacks in that the weak energy from the radiation cannot be detected with a high sensitivity.

SUMMARY OF THE INVENTION

The primary object of the present invention is to provide a micro array, which eliminates the necessity of performing an operation for setting the position of a stimulable phosphor sheet with respect to the micro array, such that the processing time may be kept short and detection sensitivity may be enhanced.

Another object of the present invention is to provide a biomolecule analyzing method, in which the micro array is utilized.

A further object of the present invention is to provide a sample analyzing method, in which the micro array is utilized.

In the present invention, the purposes for which the micro array is used are not limited to gene analyses as with a DNA chip, such as genetic expression analysis, base sequence determination, variant analysis, and polymorphism analysis, and embrace a wide variety of applications to analyses of samples, which are capable of selectively binding with multiple kinds of detecting bodies through certain reactions, the detecting bodies having been arrayed and fixed in a spot-like form on a base plate.

The present invention provides a first micro array, comprising a stimulable phosphor sheet, and multiple kinds of biomolecules arrayed and fixed on the stimulable phosphor sheet.

In the first micro array in accordance with the present invention, the multiple kinds of the biomolecules may be fixed on or within a protective layer of the stimulable phosphor sheet. Alternatively, the multiple kinds of the biomolecules may be fixed on or within a phosphor layer of the stimulable phosphor sheet. In every case, the multiple kinds of the biomolecules must be fixed at least in a manner such that they can undergo a reaction, such as hybridization, with the labeled biomolecules to bind with the labeled biomolecules. For example, the fixed biomolecules should be exposed on the surface of the stimulable phosphor sheet, such that the labeled biomolecules can come into contact with the fixed biomolecules.

In accordance with the purposes for which the micro array is used, the bodies arrayed and fixed in a spot-like form on the stimulable phosphor sheet of the micro array in accordance with the present invention are not limited to the biomolecules, and may be a wide variety of bodies which are capable of selectively binding with samples through certain reactions, depending upon the kinds of properties of the bodies. The wide variety of the bodies are herein referred to as the "detecting bodies."

Therefore, the present invention also provides a second micro array, comprising a stimulable phosphor sheet, and multiple kinds of detecting bodies arrayed and fixed on the stimulable phosphor sheet.

The present invention further provides a biomolecule analyzing method, comprising the steps of:

i) preparing a micro array, which comprises a stimulable phosphor sheet, and multiple kinds of biomolecules arrayed and fixed on the stimulable phosphor sheet, ii) bringing a labeled biomolecule, which has been labeled with an energy generating substance, into contact with the micro array to cause the labeled biomolecule to undergo hybridization with a fixed biomolecule, which is among the multiple kinds of the biomolecules arrayed and fixed on the stimulable phosphor sheet, iii) causing the stimulable phosphor sheet to store energy from the energy generating substance, with which the labeled biomolecule having been hybridized with the fixed biomolecule has been labeled, iv) exposing the stimulable phosphor sheet, on which the energy from the energy generating substance has been stored, to stimulating rays, which cause the stimulable phosphor sheet to emit light in proportion to the amount of energy stored thereon, and v) photoelectrically detecting the emitted light, whereby the fixed biomolecule having been hybridized with the labeled biomolecule is detected.

The present invention still further provides a sample analyzing method, comprising the steps of:

i) preparing a micro array, which comprises a stimulable phosphor sheet, and multiple kinds of detecting bodies arrayed and fixed on the stimulable phosphor sheet, ii) bringing a sample, which contains a plurality of constituents and has been labeled with an energy generating substance, into contact with the micro array to cause a constituent, which is among the plurality of the constituents of the sample and is capable of binding with one of the detecting bodies, to bind with the detecting body, iii) causing the stimulable phosphor sheet to store energy from the energy generating substance, with which the sample having been bound with the detecting body has been labeled, iv) exposing the stimulable phosphor sheet, on which the energy from the energy generating substance has been stored, to stimulating rays, which cause the stimulable phosphor sheet to emit light in proportion to the amount of energy stored thereon, and v) photoelectrically detecting the emitted light, whereby the kind of the detecting body having been bound with the sample is detected.

In the first micro array and the biomolecule analyzing method in accordance with the present invention, the biomolecules, which are arrayed and fixed on the stimulable phosphor sheet, may be selected from a wide variety of biomolecules, which are utilized in the array techniques, such as cDNA, oligo-DNA, other DNA's, PNA, and EST.

In the first and second micro arrays, the biomolecule analyzing method, and the sample analyzing method in accordance with the present invention, the multiple kinds of the biomolecules or the multiple kinds of the detecting bodies may be arrayed in a matrix-like form in twodimensional directions on the stimulable phosphor sheet. For example, the biomolecules or the detecting bodies may be arrayed in a square lattice-like form or a rhombic lattice-like form. The unit lattice is not limited to a quadrilateral shape and may be a hexagonal shape, or the like. Specifically, a plurality of dots of the biomolecules or the detecting bodies may be arrayed at a high density in a narrow area. Also, there may be several lattice points at which the biomolecules or the detecting bodies are not located.

Ordinarily, as the biomolecule, which is labeled with the energy generating substance, cDNA, genome DNA, mRNA, total RNA, one of the other RNA's, dNTP, PNA, or the like, is utilized. However, the biomolecule, which is labeled with the energy generating substance, is not limited to the above-enumerated biomolecules.

The term "hybridization" as used herein means the at biochemically defined hybridization with which a complementary base sequence forms a duplex strand, and the other ordinary binding reactions, such-as the binding with specific binding, which occur such that the bound biomolecule may not be removed with washing.

Examples of the binding through certain reactions include the binding through various kinds of affinity.

With the first and second micro arrays, the biomolecule analyzing method, and the sample analyzing method in accordance with the present invention, it is not necessary to perform an operation for superposing a base plate and a stimulable phosphor sheet as with the conventional techniques, and to perform an operation for accurately setting the positions of the base plate and the stimulable phosphor sheet. Therefore, automatic processing can be performed easily, and the time required to perform the processing can be kept short. Also, in cases where the processing is to be performed manually, the number of the processing steps can be reduced, and the time required to perform the processing can be kept short.

Further, it is not necessary to perform the step for bringing the stimulable phosphor sheet into close contact with the base plate and causing the energy from the radiation to be stored on the stimulable phosphor sheet, and the energy generating substance, with which the biomolecule or the sample has been labeled, is located in the immediate vicinity of the stimulable phosphor sheet. Therefore, the weak energy from the radiation can be detected with a high sensitivity. Accordingly, the size of the dots of the biomolecules or the detecting bodies can be reduced even further, and the time required to perform the hybridization or the binding can be kept short.

BRIEF DESCRIPTION OF THE DRAWINGS

FIG. 1 is a perspective view showing an example of a stimulable phosphor sheet employed in an embodiment of the biomolecule analyzing method in accordance with the present invention.

DESCRIPTION OF THE PREFERRED EMBODIMENTS

Figure 2:
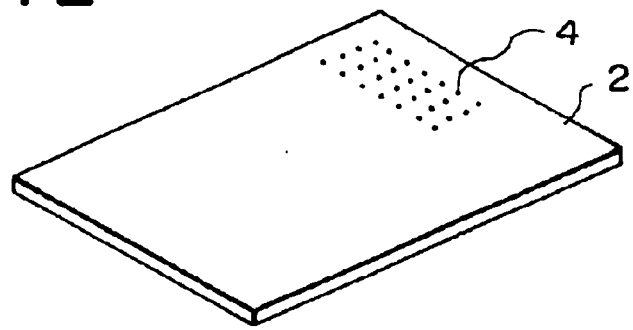
FIG. 2 is an explanatory perspective view showing how multiple kinds of biomolecules are arrayed and fixed in a matrix-like form on the surface of the stimulable phosphor sheet.

The present invention will hereinbelow be described in further detail with reference to the accompanying drawings.

In FIG. 1, reference numeral 2 represents a stimulable phosphor sheet (i.e., an imaging plate). The stimulable phosphor sheet 2 comprises a polyester substrate and a phosphor layer overlaid on the polyester substrate. The phosphor layer comprises a binder and BaFX phosphor particles (where X represents a halogen) dispersed with a high density in the binder. The surface of the phosphor layer is covered with a protective layer.

Multiple kinds of biomolecules are arrayed and fixed in a matrix-like form on the protective layer of the stimulable phosphor sheet 2. The step of arraying and fixing the multiple kinds of biomolecules on the protective layer of the stimulable phosphor sheet 2 is performed with a known technique. Specifically, preliminary treatment is firstly performed, in which the surface of the protective layer of the stimulable phosphor sheet 2 is dipped in a poly-L-lysine solution and dried to form a coating layer. Thereafter, as illustrated in FIG. 2, a solution containing biomolecules, such as cDNA's, is arrayed and fixed in a dot-like form on the surface of the stimulable phosphor sheet 2 by the utilization of a commercially available spotter device. In this manner, the cDNA dots 4, 4, . . . are arrayed and fixed in a matrix-like form on the stimulable phosphor sheet 2.

Thereafter, poly(A)RNA, which has been prepared by utilizing RNA extracted from cells to be analyzed, is labeled with a radioactive isotope (RI), and an RI-labeled RNA biomolecule 6 is thus obtained. Also, a solution containing the RI-labeled RNA biomolecule 6 is prepared. In this case, a radioactive isotope, such as $^{32}$P, $^{33}$P, or $^{14}$C, may be utilized.

Figure 3:
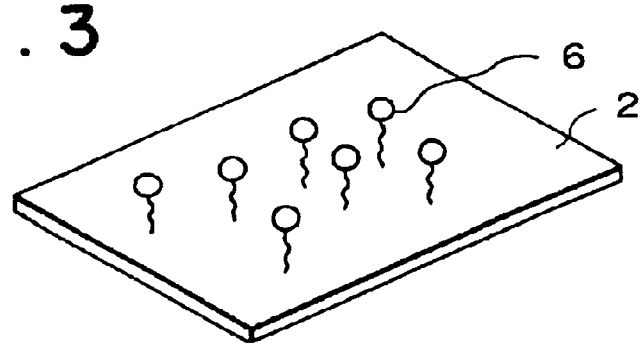
FIG. 3 is an explanatory perspective view showing how a hybridization step is performed.
Figure 4:
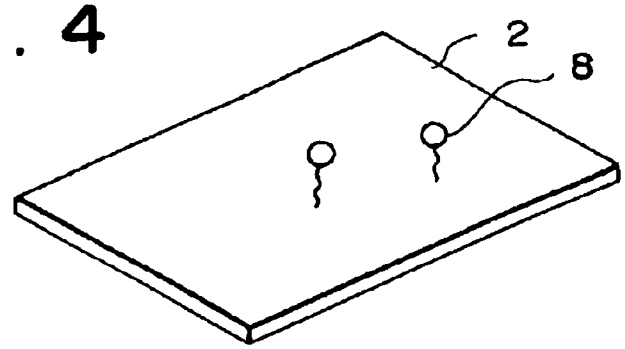
FIG. 4 is an explanatory perspective view showing a state after hybridization is performed.

Thereafter, as illustrated in FIG. 3, the stimulable phosphor sheet 2, on which the cDNA dots 4, 4, . . . have been fixed, is dipped in the solution containing the RI-labeled RNA biomolecule 6. In this manner, the cDNA dots 4, 4, . . . having been fixed on the stimulable phosphor sheet 2 and the RI-labeled RNA biomolecule 6 are subjected to hybridization. The surface of the stimulable phosphor sheet 2 is then washed. With the washing, the RI-labeled RNA biomolecule 6, which was not hybridized with the cDNA dots 4, 4, . . . having been fixed on the stimulable phosphor sheet 2, is removed. As a result, as illustrated in FIG. 4, only the RI-labeled RNA biomolecule 8, which has been hybridized with a cDNA dot 4 having been fixed on the stimulable phosphor sheet 2, remains on the stimulable phosphor sheet 2.

The entire area of the stimulable phosphor sheet 2 is then exposed to visible light, and information on the stimulable phosphor sheet 2 is erased. Thereafter, the stimulable phosphor sheet 2 is left to stand at a dark place and is caused to store energy from radiation radiated out from the RI-labeled RNA biomolecule 8, which has been hybridized with the cDNA dot 4 fixed on the stimulable phosphor sheet 2.

Thereafter, the entire area of the surface of the stimulable phosphor sheet 2 is exposed to a reading laser beam 10, which causes the stimulable phosphor sheet 2 to emit light in proportion to the amount of energy stored thereon during its exposure to the radiation. As a result, the light is emitted from the site on the stimulable phosphor sheet 2, which site was exposed to the radiation radiated out from the radioactive isotope acting as the label of the RI-labeled RNA biomolecule 8 that has been hybridized with the cDNA dot 4 on the stimulable phosphor sheet 2 during the hybridization, and which site has thus stored the energy from the radiation. The light emitted from the site on the stimulable phosphor sheet 2 is photoelectrically detected with a photomultiplier (PMT), and an electric signal is thereby obtained from the PMT. The electric signal is fed into a computer C, and the information representing the position of the light emission is stored in the computer C.

Figure 5:
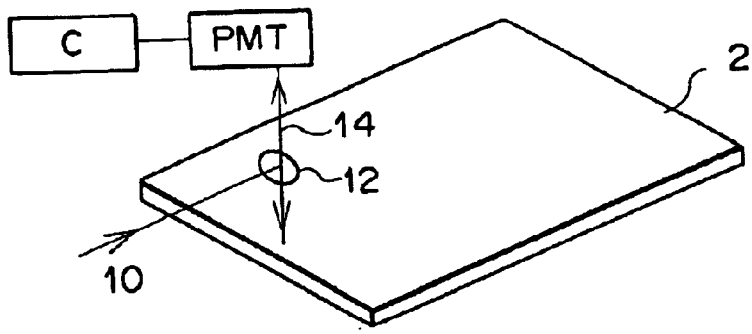
FIG. 5 is an explanatory perspective view showing how the stimulable phosphor sheet is exposed to a reading laser beam, which cause it to emit light in proportion to the amount of energy stored thereon.
Figure 6:
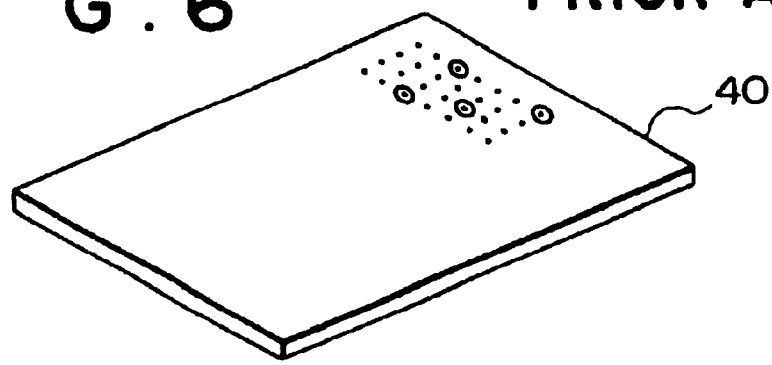
FIG. 6 is an explanatory perspective view showing a base plate of a conventional micro array.
Figure 7:
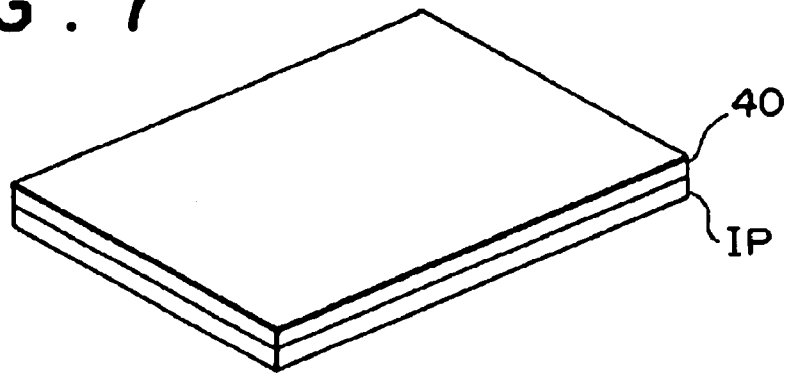
FIG. 7 is an explanatory perspective view showing a step of superposing a stimulable phosphor sheet upon the base plate of the conventional micro array and exposing the stimulable phosphor sheet to radiation.
Figure 8:
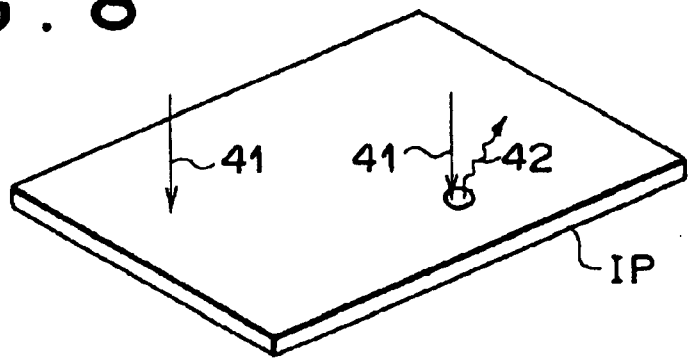
FIG. 8 is an explanatory perspective view showing a step of reading out an image having been stored on the stimulable phosphor sheet.

As illustrated in FIG. 5, by way of example, the reading laser beam 10 is reflected by a semi-transparent mirror or a dichroic mirror 12 onto the surface of the stimulable phosphor sheet 2. Also, light 14 emitted by the stimulable phosphor sheet 2 is passed through the mirror 12 and is caused to impinge upon the PMT.

The information representing the position of the light emission is compared with previously stored information, which represents which cDNA is located at which site on the stimulable phosphor sheet 2. In this manner, the cDNA, which was hybridized with the RNA extracted from the cells, and the cDNA, which was not hybridized with the RNA extracted from the cells, are specified.

In the embodiment described above, the protective layer is formed on the surface of the phosphor layer of the stimulable phosphor sheet 2, and the cDNA dots 4, 4, . . . are fixed on the surface of the protective layer. Alternatively, a permeable protective layer may be employed, and the cDNA dots 4, 4, . . . may be fixed within the protective layer.

As another alternative, a stimulable phosphor sheet having no protective layer may be employed, and the cDNA dots 4, 4, . . . may be fixed on the surface of the phosphor layer of the stimulable phosphor sheet. As a further alternative, a stimulable phosphor sheet having no protective layer may be employed, the phosphor layer of the stimulable phosphor sheet may be constituted of a permeable layer having pores, and the cDNA dots 4, 4, . . . may be fixed within the phosphor layer of the stimulable phosphor sheet. In such cases, the phosphor layer should preferably be formed from phosphor particles having the a coated surface, such that the phosphor of the phosphor layer may not be damaged.

In the embodiment described above, the stimulable phosphor sheet 2 comprises the polyester substrate and the phosphor layer overlaid on the polyester substrate. Also, the phosphor layer of the stimulable phosphor sheet 2 comprises the binder and the BaFX phosphor particles (where X represents a halogen) dispersed with a high density in the binder. Alternatively, one of various known stimulable phosphor sheets may be employed.

In addition, all of the contents of Japanese Patent Application Nos. 11(1999)-211308 are incorporated into this specification by reference.

What is claimed is:

1. A micro array, comprising a stimulable phosphor layer provided on a substrate, wherein affixed within said phosphor layer is an array of a series of selected biomolecules, wherein the location of each selected biomolecule in said series, within said phosphor layer, is known.

2. A micro array, comprising a stimulable phosphor layer provided on a substrate and a protective layer provided on said stimulable phosphor layer, wherein affixed within said protective layer is an array of a series of selected biomolecules, wherein the location of each selected biomolecule in said series, within said protective layer, is known.

3. The micro array of claim 2, wherein said protective layer is a poly-L-lysine protective layer.

4. The micro array of claim 1 or 2, wherein said biomolecule is an oligonucleotide.

5. A method for analyzing a biomolecule, comprising the steps of:
(i) preparing a micro array, wherein said micro array comprises a stimulable phosphor layer provided on a substrate, wherein affixed within said phosphor layer is an array of a series of selected biomolecules, wherein the location of each selected biomolecule in said series, within said phosphor layer, is known,
(ii) contacting the micro array of step (i) with a labeled biomolecule, to cause the labeled biomolecule to be bound to one or more members of the series of selected biomolecules, wherein said labeled biomolecule is labeled with an energy generating substance,
(iii) exposing the resulting micro array of step (ii) to visible light to thereby induce the release of energy from phosphor molecules in the stimulable phosphor layer,
(iv) placing the micro array of step (iii) in a dark place to thereby cause the stimulable phosphor layer to store energy released from the energy generating substance,
(v) exposing the resulting micro array of step (iv) to stimulating rays which cause the stimulable phosphor layer to emit light in proportion to the amount of energy stored therein,
(vi) photoelectrically detecting the resulting emitted light from step (v) as a signal, so as to detect the one or more members of the series of selected biomolecules which are bound to the labeled molecule, and
(vii) determining the identity of the one or more members of the series of selected biomolecules bound to the labeled biomolecule by comparing the location of the detected signal in the micro array to the location of said one or more members of the series of selected biomolecules based on previously stored positional information.

6. A method for analyzing a biomolecule, comprising the steps of:
(i) preparing a micro array, wherein said micro array comprises a stimulable phosphor layer provided on a substrate and a protective layer provided on said phosphor layer, wherein affixed within said protective layer is an array of a series of selected biomolecules, wherein the location of each selected biomolecule in said series, within said protective layer, is known,
(ii) contacting the micro array of step (i) with a labeled biomolecule, to cause the labeled biomolecule to be bound to one or more members of the series of selected biomolecules, wherein said labeled biomolecule is labeled with an energy generating substance,
(iii) exposing the resulting micro array of step (ii) to visible light to thereby induce the release of energy from phosphor molecules in the stimulable phosphor layer,
(iv) placing the micro array of step (iii) in a dark place to thereby cause the stimulable phosphor layer to store energy released from the energy generating substance, (v) exposing the resulting micro array of step (iv) to stimulating rays which cause the stimulable phosphor layer to emit light in proportion to the amount of energy stored therein, (vi) photoelectrically detecting the resulting emitted light from step (v) as a signal, so as to detect the one or more members of the series of selected biomolecules which are bound to the labeled molecule, and (vii) determining the identity of the one or more members of the series of selected biomolecules bound to the labeled biomolecule by comparing the location of the detected signal in the micro array to the location of said one or more members of the series of selected biomolecules based on previously stored positional information.

7. A micro array, comprising a stimulable phosphor layer provided on a substrate, wherein affixed within said phosphor layer is an array of a series of selected detecting bodies, wherein the location of each selected detecting body in said series, within said phosphor layer, is known.

8. A micro array, comprising a stimulable phosphor layer provided on a substrate and a protective layer provided on said stimulable phosphor layer, wherein affixed within said protective layer is an array of a series of selected detecting bodies, wherein the location of each selected detecting body in said series, within said protective layer, is known.

9. The micro array of any one of claims 1, 2, 7 or 8, wherein said substrate is polyester.

10. A method for analyzing a sample, comprising the steps of:

(i) preparing a micro array, wherein said micro array comprises a stimulable phosphor layer provided on a substrate, wherein affixed within said phosphor layer is an array of a series of selected detecting bodies, wherein the location of each selected detecting body in said series, within said phosphor layer, is known, (ii) contacting the micro array of step (i) with a sample, wherein said sample comprises a plurality of constituents which are labeled with an energy generating substance, to cause a constituent in said sample to be bound to one or more members of the series of selected detecting bodies, (iii) exposing the resulting micro array from step (ii) to visible light to thereby induce the release of energy from phosphor molecules in the stimulable phosphor layer, (iv) placing the micro array of step (iii) in a dark place to thereby cause the stimulable phosphor layer to store energy release from the energy generating substance, (v) exposing the resulting micro array of step (iv) to stimulating rays which cause the stimulable phosphor layer to emit light in proportion to the amount of energy stored therein, (vi) photoelectrically detecting the resulting emitted light from step (v) as a signal, so as to detect a labeled constituent of the sample which is bound to a detecting body, and (vii) determining the identity of a labeled constituent of the sample by comparing the location of the detected signal in the micro array to the location of said one or more members of the selected detecting bodies based on previously stored positional information.

11. A method for analyzing a sample, comprising the steps of:

(i) preparing a micro array, wherein said micro array comprises a stimulable phosphor layer provided on a substrate and a protective layer provided on said phosphor layer, wherein affixed within said protective layer is an array of a series of selected detecting bodies, wherein the location of each selected detecting body in said series, within said protective layer, is known, (ii) contacting the micro array of step (i) with a sample, wherein said sample comprises a plurality of constituents which are labeled with an energy generating substance, to cause a constituent in said sample to be bound to one or more members of the series of selected detecting bodies, (iii) exposing the resulting micro array from step (ii) to visible light to thereby induce the release of energy from phosphor molecules in the stimulable phosphor layer, (iv) placing the micro array of step (iii) in a dark place to thereby cause the stimulable phosphor layer to store energy release from the energy generating substance, (v) exposing the resulting micro array of step (iv) to stimulating rays which cause the stimulable phosphor layer to emit light in proportion to the amount of energy stored therein, (vi) photoelectrically detecting the resulting emitted light from step (v) as a signal, so as to detect a labeled constituent of the sample which is bound to a detecting body, and (vii) determining the identity of a labeled constituent of the sample by comparing the location of the detected signal in the micro array to the location of said one or more members of the selected detecting bodies based on previously stored positional information.

12. The method of any one of claims 5, 6, 10 and 11, wherein said substrate is polyester.

13. The method of claim 5 or 6, wherein said biomolecules are oligonucleotides.

14. The method of claim 6, wherein said protective layer is a poly-L-lysine protective layer.

* * * * *